US005360002A

United States Patent [19]

Smith

[11] Patent Number: 5,360,002

[45] Date of Patent: * Nov. 1, 1994

[54] SINGLE PATIENT USE DISPOSABLE CARBON DIOXIDE ABSORBER

[76] Inventor: Charles A. Smith, 625 E. Market, Louisville, Ky. 40202

[ * ] Notice: The portion of the term of this patent subsequent to Sep. 1, 2009 has been disclaimed.

[21] Appl. No.: 818,658

[22] Filed: Oct. 28, 1991

Related U.S. Application Data

[63] Continuation-in-part of Ser. No. 699,485, May 13, 1991, Pat. No. 5,228,435.

[51] Int. Cl.⁵ .................. A62B 7/10; A62B 23/02; A62B 19/00
[52] U.S. Cl. .................. 128/205.28; 128/205.12
[58] Field of Search .................. 128/205.12, 204.18, 128/205.23, 202.26, 205.27, 205.28, 205.29

[56] References Cited

U.S. PATENT DOCUMENTS

| 2,090,358 | 8/1937 | Reiter | 128/205.28 |
| 2,614,561 | 10/1952 | Fox | 128/205.28 |
| 2,675,885 | 4/1954 | Fox | 128/205.28 |
| 2,918,356 | 12/1959 | Hay | 128/205.28 |
| 3,240,567 | 3/1966 | Caparreli et al. | 128/205.28 |
| 3,566,867 | 3/1971 | Dryden | 128/205.28 |
| 3,707,965 | 1/1973 | Guzay | 128/205.28 |
| 3,713,440 | 1/1973 | Nicholes | 128/205.12 |
| 3,738,360 | 6/1973 | Dryden | 128/205.28 |
| 3,923,057 | 12/1975 | Chalon | 128/205.28 |
| 3,980,081 | 9/1976 | Cotabish et al. | 128/202.26 |
| 4,750,485 | 6/1988 | Bartos | 128/205.24 |
| 5,016,628 | 5/1991 | Lambert | 128/205.28 |
| 5,038,768 | 8/1991 | McGoff et al. | 128/205.28 |

FOREIGN PATENT DOCUMENTS 1424628  2/1976  United Kingdom ........... 128/204.17

Primary Examiner—Kimberly L. Asher

[57] ABSTRACT

The invention relates to a disposable single patient use device for conditioning air administered to a patient under anesthesia. The apparatus includes an air impervious independently supported container located in immediate proximity to the patient with an inlet and an outlet opening and a mass of granular carbon dioxide absorption material disposed within the container in flow communication with the inlet and outlet openings. The exhalent breath of the patient, laden with carbon dioxide, enters the container and contacts the carbon dioxide absorption material whereupon the carbon dioxide is absorbed with the resultant instantaneous generation of heat and water vapor. The size of the container and the amount of carbon dioxide absorption material is selected such that the normal breathing of the patient causes air to be warmed, humidified, freed of carbon dioxide and recirculated to the patient upon the second and subsequent breaths. The size of the container, the amount of carbon dioxide absorbing material and the location of the container in immediate proximity to the patient also combine to provide a self-regulating feature to the system such that air, at an acceptable humidity and carbon dioxide level and temperature, will be delivered compatible with the patient's breathing rate and tidal volume.

5 Claims, 2 Drawing Sheets

SINGLE PATIENT USE DISPOSABLE CARBON DIOXIDE ABSORBER

This application is a continuation-in part of Ser. No. of 07/699,485, filed May 13, 1991, now U.S. Pat. No. 5228435.

BACKGROUND OF THE INVENTION

The present invention relates to carbon dioxide absorption devices used in breathing assistance systems and more particularly to recirculatory aided respiration systems for surgical or other medical applications, usually involving anesthesia.

In using recirculating breathing assistance systems, particularly with patients who are experiencing breathing difficulty because of trauma, surgical procedures, anesthesia, or other reasons, it is generally desirable to provide heated and humidified air to the patient. Warm, humidified air prevents "drying out" of the mucociliary tissues of the patient's respiratory system, and reduces patient heat loss that results from evaporation of water vapor from the lungs. It is also desirable that the air provided to the patient be relatively free of any contamination, especially contamination which may result from previous use of the system by another patient.

Complicated, proven hazardous, and relatively expensive apparatus have often, been employed to condition the air supplied to a patient in a recirculatory aided respiration system. Where such a system is in use for a surgery or other operating room procedure, anesthesia gases or other conditioning agents are often introduced into the stream of air inhaled by the patient. Also, any recirculation system requires the removal of carbon dioxide from the air exhaled by the patient.

Such prior art systems for warming and humidifying air supplied to a patient often require the use of water reservoirs, heaters, and complicated delivery systems including complex electrical/electronic controls. Those systems may require complex hose connections and knowledge of the control systems; they may also require a significant amount of space in the operating room. Setup of these prior art systems can be quite complicated, and the systems may require substantial capital outlay as well as costly supplies. In such previous applications, the use of heated humidifiers is prevalent in order to provide proper conditioning for the air and entrained gases supplied to the patient.

SUMMARY OF THE INVENTION

By proper utilization of the heat typically generated by the reaction of carbon dioxide with a granular absorbent material, such as soda lime, and by effective insulation, the typically expensive and often troublesome arrangements of a heated humidifier, water supply, reservoir, hose connection system, electronic monitoring and control, bulky mounting apparatus, and other generally complicated arrangements as employed in the prior art can be much simplified or eliminated. The carbon dioxide removal, heating, and humidifying functions can also be islolated from an associated anesthesia machine in disposable fashion to prevent cross contamination between patients. The capability of a single-use disposable device to warm, humidify and filter the air stream recirculated to the patient, and to provide great flexibility and convenience to medical personnel utilizing such a device is highly advantageous. One device providing some of these features and advantages is the subject matter of a pending U.S. patent application, Ser. No. 590,967, filed on Oct. 1, 1990 by the inventor of the present invention. This invention is another device that achieves the same fundamental objects in a different manner with yet additional advantages.

The present invention relates to the heating and humidification of air to be supplied to a patient which eliminates electrical/electronic humidifiers, heaters, and other related apparatus, previously listed and generally required by previous procedures, to properly condition the air before it returns to the patient. In general, a device within the scope of the present invention absorbs carbon dioxide from recirculated air mixed with anesthesia gases, and simultaneously warms and humidifies the air. The device can also include means for filtering out dust, virus and/or bacteria.

Nevertheless, the devices of the invention are simple and inexpensive enough such that the complete carbon dioxide absorbing unit can be disposed of after only a single patient use.

The single patient use device of the present invention does not require the flow control valves normally included in conventional carbon dioxide absorption devices. Rather, any of the devices of the present invention may be utilized together with the elements of a conventional recirculatory aided respiration system having flow control valves, air bag, hoses, etc., to provide a carbon dioxide absorption capability for the "life" of the soda lime or other $CO_2$ absorption material, after which disposal of the single use unit of the present invention and replacement by a new disposable unit ensues.

An important feature of the present invention is that the only portion of the aided respiration system which is discarded is that portion which ceases to be operational, i.e., the carbon dioxide absorbing material itself and the container and hoses. Moreover, the device provides all of the features of a conventional aided respiration system having a carbon dioxide absorber with the additional feature that replacement of the spent soda lime granules is performed quickly and easily with the disconnection and reconnection of only two hoses.

The disposable device according of the present invention is thermally self regulating; as more air is circulated, the air heating and humidification increases. That is, the amount of heat generated in the exothermic reaction associated with $CO_2$ absorption correspondingly increases because of the increased quantity of carbon dioxide produced by the patient.

Specifically the self-regulating aspect of the present invention derives from the fact that the source of heat and humidity is a direct consequence of the exothermic chemical reaction of carbon dioxide and the soda lime. Carbon dioxide is derived from the metabolic reaction at the biologic cell level and is delivered to the ventilating gas stream at the alveolar area of the patients lung. The amount of $CO_2$ produced is dependant on the patient's body weight and activity, which is minimal during surgery. Consequently it can be seen that $CO_2$ is delivered in a metered dose as part of a tidal volume of gas passing from the patient to the respiratory system 10 and then on to the unit 40 at a rate controlled by the anesthesiologist. The reaction between $CO_2$ and soda lime produces 13,500 calories per gram molecular weight (mole) of $CO_2$ (22.4 liters). Thus a known tidal volume of known $CO_2$ content combines with a preselected amount of soda lime at a known reaction rate.

Consequently the device can be considered to be self-regulating.

Insulation is preferably disposed around the device, the hoses, and other elements of the system to reduce heat loss. One such insulating device for hoses is described and taught in U.S. patent application Ser. No. 07/019,248 filed Feb. 26, 1987 by the inventor Charles A. Smith and incorporated herein by reference.

Accordingly, the invention relates to a single-patient-use disposable device for removing carbon dioxide from, and increasing the moisture content and temperature of, air delivered to a patient connected in a recirculatory aided respiration system which system includes an anesthesia machine having an inlet flow control valve and an outlet flow control valve. The system also includes an exhalation conduit through which a stream of air exhaled by the patient flows to the inlet valve of the anesthesia machine, and an inhalation conduit through which a stream of air from the outlet valve of the anesthesia machines flows to be inhaled by the patient.

The device in its preferred form comprises a sealed, transparent, air impervious container having an inlet opening and an outlet opening, and a mass of granular soda lime or other carbon dioxide absorbing material whereby air passing through the material to remove the carbon dioxide will be warmed, humidified and filtered.

Specifically the invention includes in a recirculatory aided respiration system for patients, the improvement of a disposable single-patient use apparatus for conditioning air administered to a patient under anesthesia including an air impervious container located in immediate proximity to the patient having an inlet opening and an outlet opening, a mass of granular carbon dioxide absorption material disposed within the container in flow communication with the inlet opening and outlet opening whereby air laden with carbon dioxide entering the container contacts the carbon dioxide absorption material and whereupon carbon dioxide is absorbed therein with the resultant generation of heat and water vapor. The size of the container and the amount of carbon dioxide absorption material is selected such that the normal breathing of a patient causes air to be freed of carbon dioxide and thus available to be recirculated to the patient at a desirable humidification level and temperature. The function of the container and material is self regulating such that air at an acceptable temperature and humidity and carbon dioxide level will be delivered compatible to the patient's breathing rate and tidal volume.

The amount of carbon dioxide absorbant material disposed within the container could be as much as 3,000 grams. However, the preferred amount is in the range of 500 to 800 grams with 550 grams being the amount most preferred within the above range. Moreover, the air impervious container is sized in the range of 1250 cc. to 1500 cc. of free air space. However, most preferred is a container size such that when it contains the absorbant material it has a free air space in the range of between 470 cc. and 1000 cc. The most preferred free air space in the container within the above range is 750 cc.

Generally the container shape is preferred to be rectangular in planar cross section with the ratio of length to width being about 2 to 1. Moreover, the container shape in the vertical direction (i.e. its depth) is determined most advantageously to terminate in a rounded bottom or distal end, most conveniently the rounded bottom is semi-circular in nature. The diameter of the circular portion is equal to the larger of the two planar dimensions, i.e. the length of the container such that the container has in essence a rounded bottom. Moreovers it has been found to be advantageous that the depth of the container be greater than the length of the container, generally a ratio of depth to width of 1.25 to 1 being preferred. Moreover, advantageously the container can be sized such that the ratio of planar cross section internal surface area to the depth of the container is approximately 2 to 1 thus, providing optimal absorbant utilization, space utilization, and optimal heat and water vapor output.

The air impervious container of the present invention also is preferably constructed of a rigid deformation resistant material. Many of the clear polymeric resinous materials have been found to be suitable. Examples include polystyrene, polypropolyene, ABS plastics, polycarbonates and the like. The advantage of using such deformation resistant material is that the sidewalls are restrained from bowing out and providing dimensional changes in the bed of absorbant material and also avoiding channeling along the sidewalls of said container. In addition, channeling along the sidewalls of the container can be avoided by adhesively affixing a layer of carbon dioxide absorbant material thereto. The result is that the sidewall is coated with the absorbent material and the remainder of the bed interfaces with such coating to provide air passageways similar to those present throughout the bed as will be seen from the drawing.

The carbon dioxide absorbant material can be selected from any one of those commercially available. One such carbon dioxide absorbtion material is produced by Dewey and Almy Chemical Division of W. R. Grace & Co. and is sold under the tradename "SODA-SORB". Generally the material includes active ingredients of sodium hydroxide and hydrated lime.

The chemical neutralization of $CO_2$ with resultant production of heat and water vapor is taught in the literature as follows:

$$CO_2 + H_2O \rightleftharpoons H_2CO_3 \qquad (i)$$

$$2H_2CO_3 + 2NA^+ + 2OH^- + 2K + 2OH^- = \\ 2NA^+ + CO_3 + 2K^+ + CO_3 + 4H_2O \qquad (ii)$$

$$CA(OH)_2 + H_2O \rightleftharpoons CA^{++} + 2OH^- + H_2O \qquad (iii)$$

$$2CA^{++} + 4OH^- + 2NA^+ + CO_3 + 2K^+ + CO_3 \rightleftharpoons 2\text{-}\\ CACO_3 + 2NA^+ + 2OH^- + 2K^+ + 2OH^- \qquad (iv)$$

In (i) the $CO_2$ dissolves at a rate governed by a number of physical chemical factors. The rate is not proportional to the partial pressure of the $CO_2$ which is in contact with the film of moisture coating the soda lime granules, but greater—because some of the $CO_2$ combines chemically with the water to form carbonic acid. The rate is directly proportional to the rate of removal of dissolved $CO_2$, or $H_2CO_3$, from solution, by reaction with hydroxyl ion (reaction ii). Thus the rapidity of removal of dissolved $CO_2$ is directly related to the availabiltiy of hydroxyl ions. Since the reaction between H+ and OH— is instantaneous, forming water, reaction (iii) and (iv) must supply additional hydroxyl ions to keep the absorption of $CO_2$ progressing. The latter two reactions are therefore rate limiting.

DESCRIPTION OF THE PRIOR ART

It has long been known that it is desirable to use a recirculatory respiratory system for anesthesizing patients. Such a system however, demands that carbon dioxide be removed from the patient's exhaled gases before they are recycled. Moreover, ideally the gas should be readministered to the patient in a warm humid condition to prevent drying of the mucus membranes and other post-operative complications. Several authors have identified this need as will be mentioned hereinafter.

One such author/inventor is Wayne W. Hay, inventor of the invention of U.S. Pat. No. 3,088,810 issued May 7, 1963. The invention of the '810 Patent is a conventional carbon dioxide absorber found in operating rooms throughout the country. The apparatus is not directed toward humidification and heating of the air although, admittedly the chemical reaction disclosed above is taking place in the carbon dioxide absorber of the invention.

Another prior art reference is entitled "Humidification of Anesthetic Gases", by Chalon et. al. published by Carl C. Thomas, publisher Bannerstone House, 301–327 East Lawrence Ave., Springfield Ill. U.S.A. 1981, Library of Congress, Catalogue Card No. 8027492. Of particular interest is FIG. 8.7 on page 76 and also FIGS. 10-2 and 11-3 showing prior art carbon dioxide removal and heating and humidification of anesthetic gases.

Similarily are D'ery et. al. have addressed the subject matter of heat and moisture in air streams in an article entitled, "Humidity in Anesthesiology II. Evolution of Heat and Moisture in the Large Carbon Dioxide Absorbers" at page 205 of *The American Anesthesioloy Society Journal* Volume 14, No. 3, May 1967. Also Krister Nelson has addressed humidification of the airways in a presentation at the Gibeck Meeting in Stockholm, March 1991 as a member of the department of Pediatric Anesthesia and Intensive Care, Ostra Sjukhuset, Gotenberg, Sweden.

Other references include an article entitled "Health Devices" published by ECRI, a non-profit agency, May 1983, Volume 12, No. 7 and U.S. Pat. No. 3,752,654.

Lastly, applicant is aware of "The Sodasorb Manual of Carbon Dioxide Absorption", published by W. R. Grace & Co, Dewey and Almy Chemical Division, copyright 1962.

The above references and the references disclosed in U.S. patent application Ser. No. 07/699,485 of which the present application is a continuation-in-part and all of the references cited in any of the foregoing constitute all of the relevant prior art known to the inventor. It should be noted that none of this prior art teaches or suggests the novel features of applicants invention which will be hereinafter more fully described and claimed.

DESCRIPTION OF THE PREFERRED EMBODIMENTS

Figure 1:
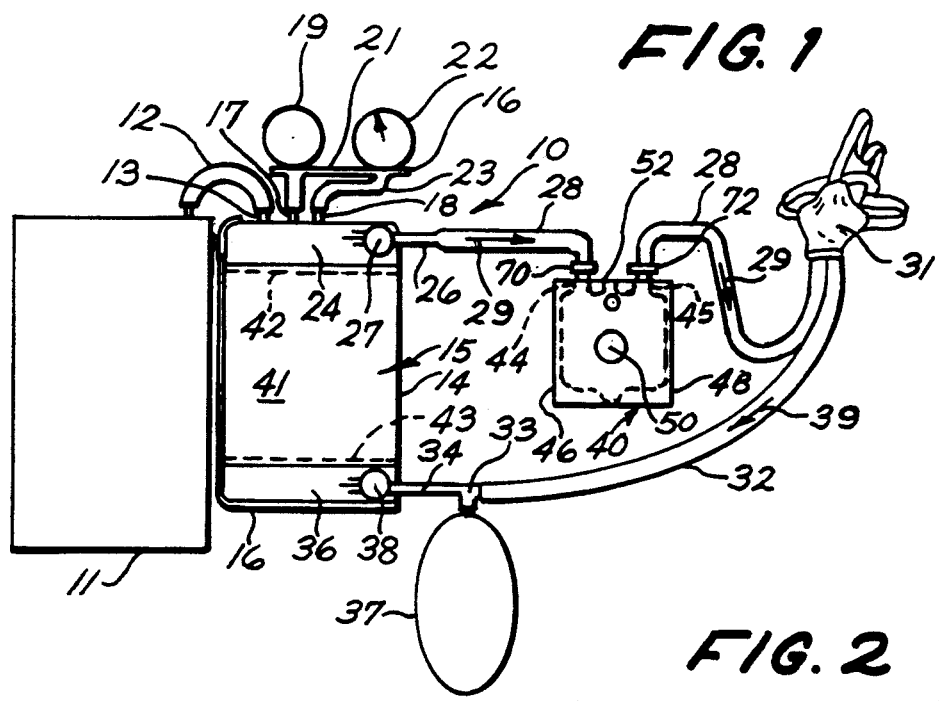
FIG. 1 is a schematic diagram of a recirculatory aided respiration system, constituting an anesthesia system, in which the present invention is incorporated.

The recirculatory aided respiration system 10 illustrated in FIG. 1, which is actually and anesthesia system, includes a conventional anesthesia or "gas" machine 11. Machine 11 is utilized to provide a desired mix of anesthetic gases through a hose 12 to a fitting 13 that is a part of the casing 14 of a device 15 that would normally serve system 10 as a carbon dioxide "absorber" which is not needed when employing the present invention. Device 15 may be mounted upon anesthesia machine 11 by suitable means such as a bracket 16, as shown schematically in FIG. 1. There are two other tubular fittings 17 and 18 at the top of the housing or canister 14 of device 15. A pressure relief valve 19 is connected by a hose 21 to fitting 17 and a manometer or other pressure indicator 22 is connected by a hose 23 to fitting 18.

The three fittings 13, 17, and 18 each communicate with an outlet chamber 24 located, in the illustrated system, in the top of device 15. Device 15 has a undirectional outlet flow control valve 27 mounted in chamber 24 to permit only outward flow of air from chamber 24 through an outlet port 26 into an inhalation hose or conduit 28, sometimes referred to as a re-breathing hose. A face mask 31 included in system 10 is connected to conduit 28 so that a patient wearing the mask can receive air, mixed with anesthetic gases, flowing to the patient in the direction indicated by arrow 29.

System 10 includes another conduit or hose 32, sometimes referred to as an exhalation or exhaust conduit. Hose 32 extends from the patient's mask 31 to a T-fitting 33 that is connected to an inlet port 34 for device 15. Port 34 is in turn connected, by a unidirectional valve 38, to an inlet chamber 36 in the bottom of device 15. A rebreathing bag 37 is also connected to the T-fitting 33. The flow of air through conduit 32 and into the inlet chamber 36 of device 15 is in the direction indicated by arrow 39.

Device 15 includes a central chamber 41 separated from the outlet chamber 24 by a wall 42 and separated from the inlet chamber 36 by another transverse wall 43. Wall 42 is provided with a plurality of apertures (not shown) to permit the flow of air from chamber 41 to chamber 24. Similarily, wall 43 includes a multiplicity of apertures (not shown) to allow the flow of air from inlet chamber 36 into central chamber 41. In a conventional system the central chamber 41 would be filled with an absorption material; the $CO_2$ absorption material typically comprises granular soda lime, though some other proprietary carbon dioxide absorption materials are occasionally used. In system 10, however, the chamber 41 of device 15 is empty.

As thus far described, system 10 would be quite conventional if the canister, device 15, were filled with soda lime or some other $CO_2$ absorber material. When the patient wearing mask 31 exhales, the exhaled air passes through conduit 32 to the inlet port 34 that leads into the inlet chamber 36 of the carbon dioxide absorption device 15 through inlet flow control, check valve 38. A part of the air exhaled by the patient may pass into the rebreathing bag 37.

When the patient wearing mask 31 inhales, air is drawn from the outlet chamber 24 of device 15 through the outlet flow control valve 27 and outlet port 26 into the inhalation hose or conduit 28. Additional air or oxygen anesthetic gases may be introduced into chamber 24 from machine 11 to pass to the patient. The pressure in the system is held to an acceptable level by relief valve 19. Other controls may be provided, usually in the anesthesia machine 11.

A major problem with the recirculatory aided respiration systems, such as the anesthesia system 10, is that the amount of carbon dioxide absorption material that they utilize is very large and acts as a heat sink and a water vapor trap. For example, device 15 would present such a problem if its chamber 41 were filled with soda lime. Moreover, the absence of filter means leads to the entrainment of dust and even larger granules of soda lime or other carbon dioxide absorption material into the air stream. This action is decidedly undesirable, particularly with respect to possible effects upon the respiratory tract of the patient wearing mask 31.

Another problem of major proportions is that device 15, in the conventional system, should be replaced for each new patient to avoid inter-patient spread of contamination. Device 15 may be treated as a single use device of this purpose, but it is really too expensive and complex for such use. Consequently, hospital and other service personnel are inclined to sterilize and recharge the device 15 with carbon dioxide absorption material and use it repeatedly. This is a poor practice. Sterilization is difficult and adds to the expense of system operation. It may also be ineffective, to the decided detriment of the next patient. And the service personnel may simply neglect to sterilize or even re-charge device 15, with potentially disastrous results.

Moreover, if such units are left standing for prolonged periods of time after an initial use unacceptably high levels of carbon monoxide are generated within the soda lime units which have a very deleterious effect on subsequent patients. In addition the absorption bed is so remote from the patient that any heat produced by the reaction between carbon dioxide and the absorbant material is completely dissipated into the downstream hoses, valves and equipment. Similarily, humidity transmitted to the air flowing through the absorption material is lost to downstream hoses, valves and equipment or condenses in conduit 28 before reaching the patient.

To minimize and eliminate these problems the recirculatory breathing assistance system is properly sized and located in the immediate proximity of the patient to take full advantage of the $CO_2$ absorption process. The present invention includes a simple in expensive, single-patient-use, disposable device 40 for removing carbon dioxide, heating, filtering and humidifying the air delivered to the patient wearing mask 31. This device 40 is shown interposed in series in the inhalation conduit 28.

The $CO_2$ absorption device 40 includes container 48 having an air inlet 44 and an air outlet 45, through which the air enters and exits while passing through the recirculation circuit. Container 48 is preferably made from two pieces of transparent rigid deformation resistant material which are sealed together, the seal providing openings 44 and 45 for communication between the outside and inside of the container.

Figure 3:
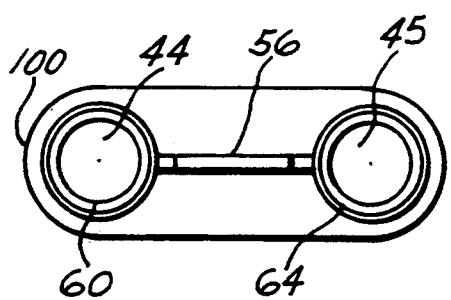
FIG. 3 is a detail sectional view taken approximately as indicated by line 3—3 in FIG. 2.
Figure 4:
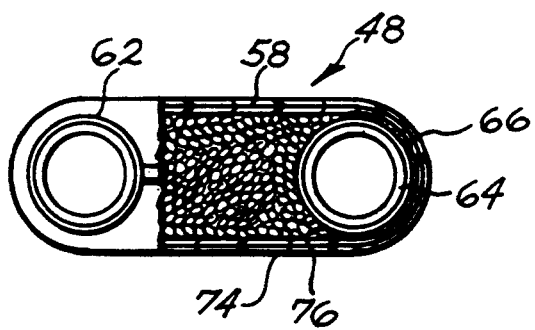
FIG. 4 is a detail sectional view taken approximately as indicated by line 4—4 in FIG. 2.
Figure 2:
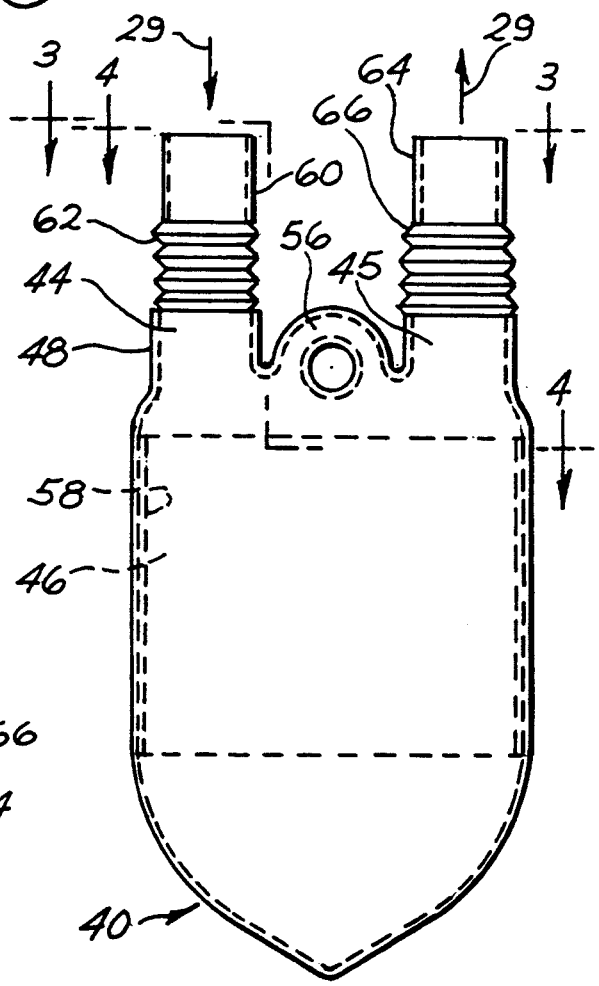
FIG. 2 is an elevation view, on an enlarged scale, of a single-use disposable carbon dioxide absorption device that comprises one embodiment of the invention.

Container 48 further includes a flexible holder 56 for supporting it in an upright position from a hook or other supporting means (not shown). Suspension of the container 48 is desirable so that it does not weigh down the conduit 28. Avoidance of weighing down of the conduit is desirable because any weight on conduit 28 pulls at mask 31 and causes discomfort to the patient or may cause container 48 to become disconnected from conduit 28. Referring now to FIGS. 2, 3, and 4, the container 48 is shown in greater detail. Flexible holder 56 can be formed as a consequence of the formation of container 48 by providing excess material in the two sheets adhesively secured together or by a single projection or strap attached later. The flexible holder 56 can be disposed between the arms formed by air inlet 44 and air outlet 45, or can be attached at other suitable locations on container 48.

FIG. 4 shows in cross section an insulating layer 58 disposed on the inside of container 48.

Insulating layer 58 is preferably disposed on the inside of container 48, but could be located on the outside thereof. Very typically insulating layer 58 is made up of a closed cell foamed polymeric resinous material examples of which are foamed polyethylene, polypropolyene, ABS, or polystyrene. Although any suitable insulating material could be used. Preferably it may be desirable to adhesively secure insulating material 58 to the interior side of container 48 under conditions where the insulating layer is positioned continuous around the inner diameter of container 48 to block any potential air path between the insulating layer and the container wall which may form or exist during construction or use of the disposable device or unit 40. Insulating layer 58 may also include a layer of reflective foil, between the insulating layer and the container wall (not shown) which would tend to minimize radiant heat loss from unit 40 hereby serving to additionally maintain heat within unit 40.

Insulating material 58 advantageously includes a viewing aperture or slot 50 for observing the color change in the CO2 absorbant as it is consumed. The slot may have champhored internal edges to avoid forming an air flow path when unit 40 is filled with $CO_2$ absorbing material. In a preferred embodiment shown in FIG. 7, insulating layer 58 terminates at a point above the bottom most part of container 40, but includes one or more tabs 59 which extend from opposite sides of container 48 and project downwardly along the side walls thereof in a butting relationship at the center line of container 48 to form stabilizing and locating means 61 which prevent insulating layer 58 from sliding downwardly in container 48 when insulating layer 58 is not adhesively secured to the sidewalls of container 48.

It is important that insulating layer 58 not be permitted to extend downwardly to the full depth of container 48 since insulating layer 58 by virtue of its presence may foster an air path either on its outside surface or its inside surface. The consequence of the formation of such an air path generally leads to less effective air treatment and detrimental downstream effects on the patient.

Figure 7:
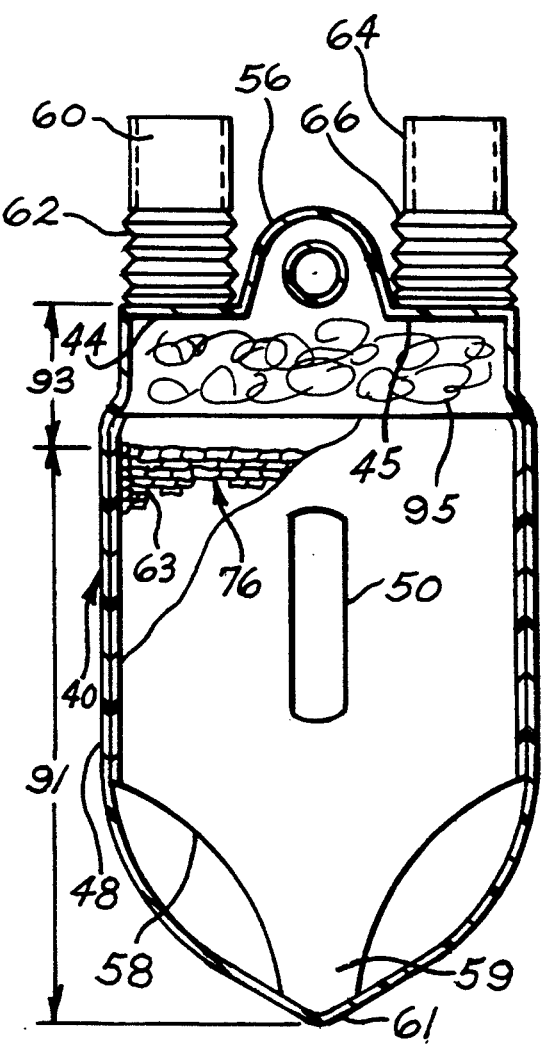
FIG. 7 is an elevation view, similar to FIG. 2 of another embodiment of the invention.

To further avoid the formation of such an air path granular carbon dioxide absorbant material can be affixed to the inside surface of the insulation layer 58 as shown in FIG. 7 at 63. Several commercially available non-toxic adhesive materials are available which are suitable for such purpose. One such adhesive is manufactured by Ross Chemical Corp. and sold under the tradename Wellbond. It should be understood that although it is desirable to affix the absorbant material on the entire inside surface of the insulating layer 58, only portions may be so treated.

Air inlet 44 includes a female joining member 60 attached to the air inlet 44 by a corrugated hose section 62, which may be a conventional 22 mm. hose. Similarily, air outlet 45 includes a male joining member 64, attached to the air outlet 45 by a section of corrugated hose 66, which may also be a conventional 22 mm. hose. Corrugated hoses 62, 66 provide flexibility to the connection of the joining members 60, 64 to the conduit 28 or 32.

As will be shown below, it is important that the air inlet 44 and air outlet 45 be differentiated. Accordingly, disposing a female joining member 60 at air inlet 44 and a male joining member 64 at air outlet 45 ensures only proper connection will be made of the device 40 into the conduit 28 of system 10. For example, to connect a device 40 into a system 10, a conduit hose 28 includes a connection (not shown) within its length of a male member within a female member, shown in FIG. 1 as 70 and 72, respectively. The connection of members 70, 72 provides a continuous passageway for an airstream through conduit 28. That connection is first broken, and the male member 70 is inserted into female joining member 60 and the female member 72 is disposed over male joining member 64, thus once again completing the air flow circuit through conduit 28. A connection of the separate sections of conduit 28 to each other may thus be temporarily broken for insertion of device 40 without creating stress to the breathing cycle of the patient.

Male and female joining members 64, 60 are thus associated with each section of conduit 28. Each of these can only be fitted onto the joining members 72, 70 in one way, thus ensuring that the connection of the device is made properly. Such a system also provides flexibility in that use of the device 40 in system 10 may be omitted if air purification is not desirable.

Moreover such a system permits very rapid error free disconnection of a spent unit and replacement with a fresh unit during an operation. It is not required that a female joining member 60 be associated with the air inlet 44 and a male joining member 64 be associated with the air outlet 45. The opposite relationship may be used even though such an arrangement may be contrary to conventional practice; the only important consideration being the consistency of the connections to ensure correct operation of the device 40, as will be explained below.

Figure 5:
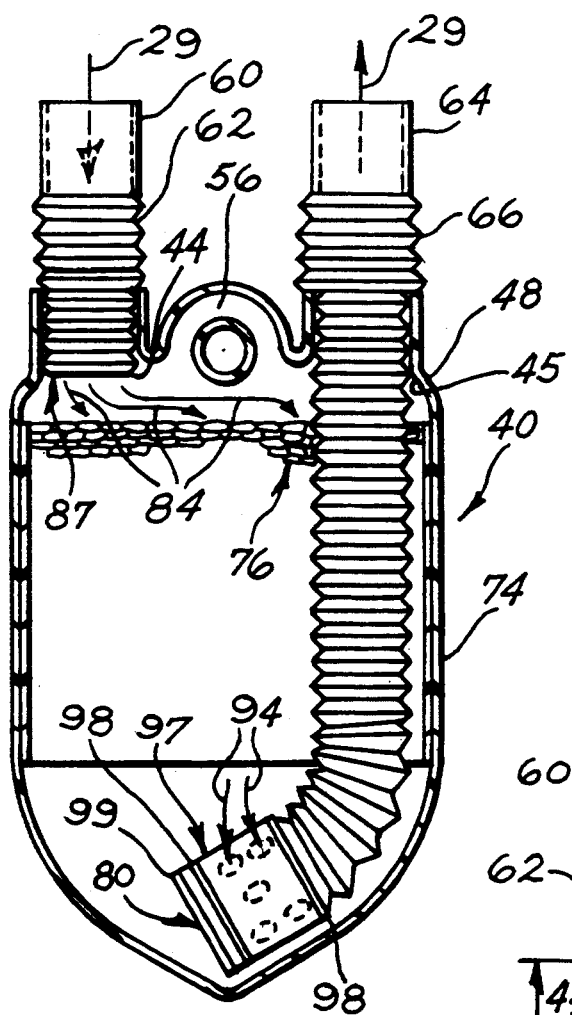
FIG. 5 is a sectional elevation view of the carbon dioxide absorber device of FIGS. 2-4.
Figure 6:
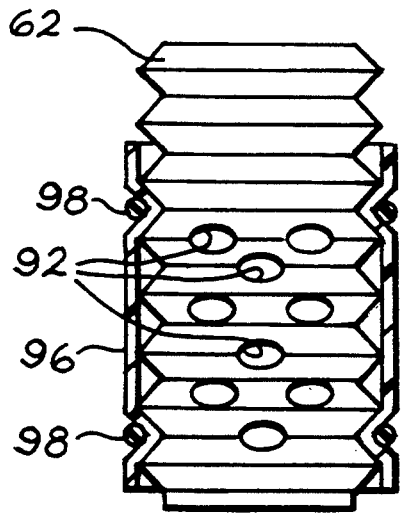
FIG. 6 is a detail view, on an enlarged scale, partly in cross-section, of a portion of the device of FIGS. 2-5.

Referring now to FIGS. 4 and 5, detail sectional views of the device 40 are shown, partially illustrating the passively operating parts of the device 40. Similar elements shown in greater detail or in full configuration will be identified by identical numerals between the respective Figures. FIG. 4 is a detail sectional view taken along line 4—4 of FIG. 3, and showing in cross section the wall 74 of container 48, insulating layer 58, and air impervious hose means or corrugated hoses 62, 66. Disposed between the corrugated hoses 62 and 66 are granules 76 of an absorbant material which absorbs carbon dioxide from the airstream flowing through the device 40. The $CO_2$ absorbant material may be soda lime or the like as is described above.

Referring now to FIG. 5, a partial sectional elevational view of the carbon dioxide absorber device 40 is illustrated, showing both ends of each of the corrugated hoses 62, 66. Female joining member 60 defines one end of corrugated hose 62 and provides an air inlet 44 into the device 40. Similarily, the male joining member 64 defines one end of the corrugated hose 66 which provides for an air outlet 45 from the device 40. An airstream outflow opening 80 defines the other end of corrugated hose 66.

As shown in FIG. 5, corrugated hose 66 extends well into the space bounded by the container 48, and the airstream outflow opening 80 is disposed as far as possible from the airstream inflow opening 78. Arrows 84 indicate the flow of air into and through the granular material 76. The construction of nonwoven fiber material 96 is set forth in greater detail in U.S. patent application No. 07/674,682, filed on Mar. 21, 1991, having common inventorship with the present invention. The disclosure of that application is incorporated herein by reference.

Outflow opening means 80 has outflow apertures 92 which permit the outflow of the airstream from the granular material 76 into the opening means 80 as indicated by arrows 94. A filter means 96 covers outflow opening means 80 and is held in place by means of rubber bands 98.

As the arrows 84 and 94 indicate, the airstream must flow into and between the granular material 76 and must flow from the container 48 and into corrugated hose 66 through outflow apertures 92. As will be explained below, container 48 is a hermetically sealed enclosure in which the inlet 44 and outlet 45 are sealed to the corrugated hoses 62 and 66 as is the edge 100 of the container 48. The airstream path, as shown by arrows 84 and 94, requires that the air pass through as much as possible of the granular material 76 in container 48. This expends as much as possible of the carbon dioxide absorbent capability of the granular material 76 because most of the material 76 comes into contact with the passing airstream.

As a preferred embodiment the present invention contemplates that hose 66 may terminate in a bacteria filter 97 which is in flow communication therewith. Several bacteria filters can be utilized as is are common in the art. One such filter, commercially available is identified as model 5000, manufactured by ARTEC Inc.

There are several advantages to locating a bacteria filter 97 within the container 48 surrounded by granular material 76. One of those advantages is that the bacteria filter 97 is kept at the surrounding temperature of the granular material which may exceed 110°. Consequently, the bacteria filter is positioned so the condensation of water in the filter is eliminated and its life thereby, prolonged. Moreover, the filter can be selected such that its size and mass do not constitute a significant heat sink and thereby, do not disadvantageously affect the temperature and humidity of the treated gas passing therethrough. In many applications it is advisable to provide for a screen 99 across the end of the filter to prevent any fine particles of the granular material from passing into the bacteria filter and causing it to become plugged and thereby shortening its life. If the above filter and screen system are used filter means 96 may be eliminated.

Granular material 76 is comprised of large granules of soda lime or the like. Soda lime changes color after its $CO_2$ absorbant capacity has been expended. Thus viewing aperture or slot 50 in insulating layer 58 provides a view of the granules 76 through a clear wall portion of the container 48. If the color change is sufficient to indicate that the granules no longer can absorb a sufficient amount of $CO_2$, then the complete container 48 may be removed from the system 10 by disconnecting male and female adjoining members 60 and 64 and replacing the container 48 with a new container containing fresh $CO_2$ absorbing material 76.

In the operation of the unit of the present invention, it can be seen that there are several advantageous features which constitute an improvement over the prior art. Specifically, as described earlier it becomes very simple to interpose the unit 40 in a conduit carrying air to the patient. Because the unit is sized in volume and soda lime content it is observed that initial charges of $CO_2$ containing gas into the unit cause immediate heat and moisture evolution. This heat quickly brings the $CO_2$ absorbant material to temperature and thereafter, heats the through flowing airstream to a desirable level. In addition, water vapor evolving from the reaction within unit 40 as well as water vapor coming from water added to the absorbant material during its manufacture and water of hydration all contribute to the through flowing gas stream being humidified to approximately 95%. This is contrasted to the normal humidification level between 50% and 60% for conventional apparatus of standard operating conditions. Thus drying of the mucus membranes is significantly reduced since humidification begins instantly after the unit is interposed in conduit 28. As described earlier, if approximately 650 grams of soda lime are used in unit 40 ample reserve for $CO_2$ removal is afforded since approximately 100 grams of absorbant material is required per hour for a normal operation with the average operation lasting for approximately two to three hours.

Referring again to FIG. 7, it should be noted that ideally, the absorbant material 76 advantageously does not fill the entire container 48, but rather divides the container into an upper portion and a lower portion 91 and 93, respectively. The lower portion contains the carbon dioxide absorbant material while the upper portion remains empty or may advantageously be filled with an air pervious flow dispensing material or air distribution means 95. The concept of having a manifold or air dispersing area above the carbon dioxide absorbant material plays a significant role inasmuch as the air entering conduit 62 is more evenly dispersed across the entire bed thereby, causing a more uniform penetration and utilization of the material 76. This air distribution means 95 in the upper portion 91 is but one way by which air flow is evened through the bed.

Other means to distribute the air relates to the fact that flow volume is greater near the peripheral wall of container 48 than through the center of bed 76. This is true even if a free air space is provided above the entire surface of the granular bed. The result is uneven use of the granular bed material due to the "wall effect".

The "wall effect" stems from the fact that gas flows more evenly over a smooth wall surface than through the tortuous channels formed by the carbon dioxide absorbant granules. Normally the container wall constitutes a smooth surface, thus the interface between the smooth surface of the wall and the rough granular bed offers less resistance to flow than the paths between the granules.

To even the flow volume through the bed, methods are some times employed such as ridges and baffles along the peripheral wall to retard or extend the flow path, thus promoting volume flow through the central portion of the granular bed. While somewhat effective in providing more uniform gas volume penetration over the bed surface, there still exists a differential in flow between the center and edges of the granular bed. The maximum flow rate differential between center and edge flow increases in the container with a short depth and large circumference. Proper sizing of container 48 suggests that to remedy the problem one should advantageously change the wall circumference and depth. This change can be expressed in terms of a depth to surface area ratio. In effect, deepening the container and decreasing the surface area results in more even penetration of the entire granular bed and better utilization of the material while minimizing the effect of any sidewall channeling.

In the case of course granular material such as the soda lime 76, intergranular space is quite large compared to the granule size so a relatively insignificant increase in flow resistance results when the container surface is decreased and container 40 is made deeper. The surface area to depth ratio of approximately 2 to 1 has been determined to be advantageous in the present invention, thereby providing optimum granule utilization, best space utilization, and optimal heat and water vapor output. Most preferred is a surface area to depth ratio in the range of 2.3 to 1, although other ratios have been found to be effective. In the alternative to the earlier suggestion of adhesively secured granules 76 to the inner surface of the insulation layer it is possible to texture the inner surface of container 48 or insulating layer 58 as the case may be, thereby eliminating the smooth surface present in prior art devices.

In summary then, utilization of the present invention by interposing it in a conduit 28 permits the elimination of carbon dioxide absorbant material in central chamber 41. Thereafter all of the air passing to the patient passes through container 40. Since the average tidal volume of an adult patient is approximately 750 cc and normally the time sequence for a complete inhalation and exhalation is in the ratio of one third of the time elapsed for inhalation and two thirds of the time elapsed for exhalation. Container 40 can be optimally sized to take advantage of several simultaneously occuring events, for example, if container 40 begins with approximately 750 cc. of intergranular volume and free air space, upon the first inhalation this treated air is transmitted to the patient. Residual air in the device 15 is immediately drawn into the absorber bed whereupon the carbon dioxide contained therein causes the evolution of heat and humidity. This heat and humidity serves to saturate and heat unit 40 and its contents such that upon the second inhalation and those subsequent thereto, the humidity and temperature of the air passing to the patient begins to rise. Subsequent inhalations of treated air continue to provide the patient with warmer humidified air as the unit 40 approaches equilibrium. The insulating material prevents heat loss to aid the process of heating and humidifying the air supply to the patient. Moreover, because the unit itself is compact it does not in and of itself constitute a large heat sink. Also because the bacteria filter 97 is located inside container 40, it is kept at the temperature of the granular bed therein, for optimal efficiency by elimination of condensation.

It should be noted that if the patient's tidal volume is greater than 750 cc., additional air will be drawn into unit 40 through conduit 28 from the device 15 and since the outlet conduit 62 extends well within unit 40 to the bottom portion thereof, any air drawn from conduit 28 will most assuredly be treated before it is inhaled by the patient. Thus the unit is termed self regulating since the greater the patient's tidal volume the more heat and humidity that is provided and the more air that is treated.

It should be further noted that every effort is made to avoid downstream valves and metal components which would serve as heat sinks. Moreover, advantageously the insulated hoses disclosed and claimed in patent application U.S. Ser. No. 07/593,555 can be employed.

Having thus described the invention what is claimed is:

1. In a recirculatory aided respiration system for patients, the improvement comprising; a disposable, single patient use apparatus, for conditioning air administered to a patient under anesthesia including an air impervious independently supported container located in immediate proximity to the patient having an inlet and an outlet opening, a mass of granular carbon dioxide absorption material disposed within said container in air flow communication with said inlet and outlet openings, said apparatus further including an air impervious hose means in fluid communication with said outlet opening extending inwardly into the lower portion of said air impervious container for insuring air passage through said granular material prior to said air proceeding through said outlet opening wherein said hose means contains therewith a bacteria filter located within said air impervious container said filter being surrounded by said carbon dioxide absorption material whereby the bacteria filter is warmed for improving its efficiency and whereby condensation of water vapor is avoided thereby providing for longer bacteria filter life said apparatus further comprising means for air laden with carbon dioxide entering said container contacting said carbon dioxide absorption material whereupon carbon dioxide is absorbed therein with resultant instantaneous generation of heat and water vapor, the size of the container and amount of carbon dioxide absorption material being selected such that the normal breathing of a patient causes air to be freed of carbon dioxide and available to be recirculated to the patient upon completion of the second and subsequent patient breaths at a desirable humidification level and temperature and said container and said amount of material are preselected to provide means for said container and material to be self regulating such that air at an acceptable temperature and humidity and carbon dioxide level will be delivered, compatible to the patient's breathing rate and tidal volume.

2. The apparatus of claim 1 wherein a screen is attached in fluid communication with said bacteria filter for pre-screening particles from the air exiting said air impervious container.

3. In a recirculatory aided respiration system for patients, the improvement comprising; a disposable, single patient use apparatus, for conditioning air administered to a patient under anesthesia including an air impervious independently supported container located in immediate proximity to the patient having an inlet and an outlet opening, a mass of granular carbon dioxide absorption material disposed within said container in air flow communication with said inlet and outlet openings, said apparatus including an insulating layer disposed against an inner side wall of said container which layer includes an inwardly facing surface coated with said carbon dioxide absorption material and further includes a slot for viewing the granular carbon dioxide absorption material contained within said container said slot having camphored edges thereby avoiding formation of air channels when said granular material is disposed within said container said apparatus further comprising means for air laden with carbon dioxide entering said container contacting with said carbon dioxide absorption material whereupon carbon dioxide is absorbed therein with resultant instantaneous generation of heat and water vapor, the size of the container and amount of carbon dioxide absorption material being selected such that the normal breathing of a patient causes air to be freed of carbon dioxide and available to be recirculated to the patient upon completion of the second and subsequent patient breaths at a desirable humidification level and temperature and said container and said amount of material are preselected to provide means for said container and material to be self regulating such that air at an acceptable temperature and humidity and carbon dioxide level will be delivered, compatible to the patient's breathing rate and tidal volume.

4. The container of claim 3 having upper and lower portions, wherein, the lower portion of said container is rounded to conform to the general direction of flow of air to be treated and whereby, said insulating layer extends along the side walls of the container from the upper portion to the lower portion, said insulating layer including tab projections extending downwardly from said insulation layer to form insulation layer stabilizing and locating means.

5. The apparatus of claim 4, wherein said insulation material extends from the upper portion of the air impervious container into the lower portion of said air impervious container but terminates at a point remote from the bottom of said air impervious container for prevention air flowing through said air impervious container from, following continuously along a side wall without at some point contacting granular carbon dioxide absorption material.

* * * * *